(12) United States Patent
Shinmyo et al.

(10) Patent No.: US 7,049,486 B2
(45) Date of Patent: May 23, 2006

(54) METHOD OF INDUCING GENE EXPRESSION IN PLANT AND THE PLANT TREATED THEREBY

(75) Inventors: Atsuhiko Shinmyo, Nara (JP); Kou Kato, Kyoto (JP); Yasuhiro Yamada, Osaka (JP); Takuya Nihira, Kyoto (JP); Takuya Shindo, Hyogo (JP)

(73) Assignee: Kaneka Corporation, Osaka (JP)

( * ) Notice: Subject to any disclaimer, the term of this patent is extended or adjusted under 35 U.S.C. 154(b) by 410 days.

(21) Appl. No.: 10/049,710

(22) PCT Filed: Jun. 15, 2001

(86) PCT No.: PCT/JP01/05096

§ 371 (c)(1),
(2), (4) Date: Sep. 4, 2002

(87) PCT Pub. No.: WO01/96581

PCT Pub. Date: Dec. 20, 2001

(65) Prior Publication Data

US 2003/0126648 A1    Jul. 3, 2003

(30) Foreign Application Priority Data

Jun. 15, 2000    (JP) .............................. 2000-180466

(51) Int. Cl.
*C12N 15/82*    (2006.01)
*C12N 15/31*    (2006.01)
*A01H 5/00*    (2006.01)

(52) U.S. Cl. ................... 800/288; 800/298; 800/317.3; 435/414; 435/419

(58) Field of Classification Search ................ 435/419, 435/414, 468; 800/288, 298, 317.3
See application file for complete search history.

(56) References Cited

U.S. PATENT DOCUMENTS 5,364,780 A    11/1994    Hershey et al.
5,614,395 A    3/1997     Ryals et al.
5,965,387 A    10/1999    Jepson et al.

FOREIGN PATENT DOCUMENTS

JP    6-339384    7/1992

OTHER PUBLICATIONS

Wilde R.J. et al. Control of gene expression in tobacco cells using a bacterial operator-repressor system. EMBO J. Apr. 1992;11(4):1251-9.*
Gatz C. et al. Regulation of a modified CaMV 35S promoter by the Tn10-encoded Tet repressor in transgenic tobacco. Mol Ge Genet. Jun. 1991;227(2):229-37.*
Gatz C. et al. Tn10-encoded tet repressor can regulate an operator-containing plant promoter. Proc Natl Acad Sci U S A. Mar. 1988;85(5):1394-7.*
Frohberg C. et al. Characterization of the interaction of plant transcription factors using a bacterial repressor protein. Proc Natl Acad Sci U S A. Dec. 1, 1991;88(23):10470-4.*
Christiane, Gatz and Ingo Lenk, "Promoters That Respond to Chemical Inducers," *Trends in Plant Sciences*, vol. 3, No. 9, Sep. 1998, pp. 352-358.
Kinoshita, Hiroshi, Hiroomi Ipposhi, Susumu Okamoto, Hiroko Nakano, Takuya Nihira and Yasuhiro Yamada, "Butyrolactone Autoregulator Receptor Protein (BarA) as a Transcriptional Regulator in Streptomyces virginiae," *Journal of Bacteriology*, vol. 179, No. 22, Nov. 1997, pp. 6986-6993.
Kinoshita, Hiroshi, Tomohiro Tsuji, Hiroomi Ipposhi, Takuya Nihira and Yasuhiro Yamada, "Characterization of Binding Sequences for Butyrolactone Autoregulator Receptors in Streptomycetes," *Journal of Bacteriology*, vol. 181, No. 16, Aug. 1999, pp. 5075-5080.
Kitani, Shigeru, Hiroshi Kinoshita, Takuya Nihira and Yasuhiro Yamada, "In Vitro Analysis of the Butyrolactone Autoregulator Receptor Protein (FarA) of *Streptomyces lavendulae* FRI-5 Reveals that FarA Acts as a DNA-Binding Transcriptional Regulator That Controls Its Own Synthesis," *Journal of Bacteriology*, vol. 181, No. 16, Aug. 1999, pp. 5081-5084.
Nakano, Hiroko, Emio Takehara, Takuya Nihira and Yasuhiro Yamada, "Gene Replacement Analysis of the *Streptomyces virginiae* barA Gene Encoding the Butyrolactone Autoregulator Receptor Reveals that BarA Acts as a Repressor in virginiamycin Biosynthesis," *Journal of Bacteriology*, vol. 180, No. 13, Jul. 1998, pp. 3317-3322.

(Continued)

*Primary Examiner*—Cynthia Collins
(74) *Attorney, Agent, or Firm*—Brinks Hofer Gilson & Lione

(57) ABSTRACT

The present invention is to provide a method which comprises providing a plant with characters of a repressor and operator both constituting a gene expression inducing system with an actinomycete autogenous regulatory factor as an inducer by gene transfer and administering the actinomycete autogenous regulatory factor to the transformed plant to thereby induce the expression of a gene placed under the control of the operator at a site of administration of the actinomycete autogenous regulatory factor. This method makes it possible to cause expression of a desired gene at a desired time and site, thus enabling even the production, in a plant, of a metabolite otherwise disadvantageous to the growth of the plant. It is also useful in preventing transformant plants from spreading through the environment by controlling the fertility thereof.

15 Claims, 4 Drawing Sheets

OTHER PUBLICATIONS

Okamoto, Susumu, Kenji Nakamura, Takuya Nihira and Yasuhiro Yamada, "Virginiae Butanolide Binding Protein from *Streptomyces virginiae*: Evidence That VbrA is Not the Virginiae Butanolide Binding Protein and Reidentification of the True Binding Protein," *The Journal of Biological Chemistry*, vol. 270, No. 20, May 19, 1995, pp. 12319-12326.

Onaka, Hiroyasu, Noriki Ando, Takuya Nihira, Yasuhiro Yamada, Teruhiko Beppu and Sueharu Horinouchi, "Cloning and Characterization of the A-Factor Receptor Gene from *Streptomyces griseus*," *Journal of Bacteriology*, vol. 177, No. 21, Nov. 1995, pp. 6083-6092.

Waki, Miyoko, Takuya Nihira and Yasuhiro Yamada, "Cloning and Characterization of the Gene (farA) Encoding the Receptor for an Extracellular Regulatory Factor (IM-2) From Streptomyces sp. Strain FRI-5," *Journal of Bacteriology*, vol. 179, No. 16, Aug. 1997, pp. 5131-5137.

* cited by examiner

```
                              SEQUENCE LISTING

<160> NUMBER OF SEQ ID NOS: 11

<210> SEQ ID NO 1
<211> LENGTH: 699
<212> TYPE: DNA
<213> ORGANISM: Streptomyces virginiae
<220> FEATURE:
<221> NAME/KEY: CDS
<222> LOCATION: (1)..(699)
<223> OTHER INFORMATION:
<300> PUBLICATION INFORMATION:
<301> AUTHORS: Okamoto, S., Nakamura, K., Nihira, T. and Yamada, Y.
<302> TITLE: Virginiae butanolide binding protein from Streptomyces
       virginiae.Evidence that VbrA is not the virginiae butanolide
       binding protein and re-identification of the true binding protein
<303> JOURNAL: Journal of Biological Chemistry
<304> VOLUME: 270
<305> ISSUE: 20
<306> PAGES: 12319-12326
<307> DATE: 1995-05-19
<308> DATABASE ACCESSION NUMBER: D32251
<309> DATABASE ENTRY DATE: 1994-07-19
<313> RELEVANT RESIDUES: (1)..(699)
<300> PUBLICATION INFORMATION:
<301> AUTHORS: Okamoto, S., Nakamura, K., Nihira, T. and Yamada, Y.
<302> TITLE: Virginiae butanolide binding protein from Streptomyces
       virginiae.Evidence that VbrA is not the virginiae butanolide
       binding protein and re-identification of the true binding protein
<303> JOURNAL: Journal of Biological Chemistry
<304> VOLUME: 270
<305> ISSUE: 20
<306> PAGES: 12319-12326
<307> DATE: 1995-05-19
<308> DATABASE ACCESSION NUMBER: D32251
<309> DATABASE ENTRY DATE: 1994-07-19

<400> SEQUENCE: 1 atg gca gtg cga cac gaa cgg gtg gca gtg cga cag gaa cgg gcc gtc        48
Met Ala Val Arg His Glu Arg Val Ala Val Arg Gln Glu Arg Ala Val
1               5                   10                  15 cgc acg cgg cag gcg atc gtg cgg gca gcc gcc tcg gtc ttc gac gag        96
Arg Thr Arg Gln Ala Ile Val Arg Ala Ala Ser Val Phe Asp Glu
            20                  25                  30 tac ggg ttc gag gcc gcc aca gtg gca gag atc ctc tcg cgg gcc tcg       144
Tyr Gly Phe Glu Ala Ala Thr Val Ala Glu Ile Leu Ser Arg Ala Ser
        35                  40                  45 gtc acc aag ggc gcg atg tac ttc cac ttc gct tcc aag gaa gag ctg       192
Val Thr Lys Gly Ala Met Tyr Phe His Phe Ala Ser Lys Glu Glu Leu
    50                  55                  60 gcc cgc ggc gtg ctg gcc gag cag acc ctg cac gtg gcg gtg ccg gaa       240
Ala Arg Gly Val Leu Ala Glu Gln Thr Leu His Val Ala Val Pro Glu
65                  70                  75                  80 tcc ggc tcc aag gcg cag gaa ctg gta gac ctc acc atg ctg gtc gcc       288
Ser Gly Ser Lys Ala Gln Glu Leu Val Asp Leu Thr Met Leu Val Ala
                85                  90                  95 cac ggc atg ctg cac gat ccg atc ctg cgg gcg ggc acg cgg ctc gca       336
His Gly Met Leu His Asp Pro Ile Leu Arg Ala Gly Thr Arg Leu Ala
            100                 105                 110 ctg gac cag ggg gcg gtg gac ttc tcc gac gcc aac ccg ttc ggc gag       384
```

-continued

```
tgg ggc gac atc tgc gcc cag ctc ctg gcg gag gca cag gaa cgg ggg      432
Trp Gly Asp Ile Cys Ala Gln Leu Leu Ala Glu Ala Gln Glu Arg Gly
    130                 135                 140 gag gtg ctt ccg cac gtg aac ccg aaa aag acc ggc gac ttc atc gtc      480
Glu Val Leu Pro His Val Asn Pro Lys Lys Thr Gly Asp Phe Ile Val
145                 150                 155                 160 ggc tgc ttc acc ggg ctc cag gcg gtc tcc cgg gtc acc tcc gac cgc      528
Gly Cys Phe Thr Gly Leu Gln Ala Val Ser Arg Val Thr Ser Asp Arg
                165                 170                 175 cag gac ctc ggc cac cgg atc tcg gtg atg tgg aac cac gtg ctg ccc      576
Gln Asp Leu Gly His Arg Ile Ser Val Met Trp Asn His Val Leu Pro
            180                 185                 190 agc atc gtg ccg gcg tcc atg ctg acc tgg atc gaa acc ggc gag gag      624
Ser Ile Val Pro Ala Ser Met Leu Thr Trp Ile Glu Thr Gly Glu Glu
        195                 200                 205 cgg atc ggg aag gtc gcg gcg gcg gcc gag gcc gcc gag gct gcg gag      672
Arg Ile Gly Lys Val Ala Ala Ala Ala Glu Ala Ala Glu Ala Ala Glu
    210                 215                 220 gcc tcc gag gcc gcc tcc gac gag tag                                  699
Ala Ser Glu Ala Ala Ser Asp Glu
225                 230
```

<210> SEQ ID NO 2
<211> LENGTH: 232
<212> TYPE: PRT
<213> ORGANISM: Streptomyces virginiae

<400> SEQUENCE: 2

```
Met Ala Val Arg His Glu Arg Val Ala Val Arg Gln Glu Arg Ala Val
1               5                   10                  15

Arg Thr Arg Gln Ala Ile Val Arg Ala Ala Ser Val Phe Asp Glu
            20                  25                  30

Tyr Gly Phe Glu Ala Ala Thr Val Ala Glu Ile Leu Ser Arg Ala Ser
        35                  40                  45

Val Thr Lys Gly Ala Met Tyr Phe His Phe Ala Ser Lys Glu Glu Leu
    50                  55                  60

Ala Arg Gly Val Leu Ala Glu Gln Thr Leu His Val Ala Val Pro Glu
65                  70                  75                  80

Ser Gly Ser Lys Ala Gln Glu Leu Val Asp Leu Thr Met Leu Val Ala
                85                  90                  95

His Gly Met Leu His Asp Pro Ile Leu Arg Ala Gly Thr Arg Leu Ala
            100                 105                 110

Leu Asp Gln Gly Ala Val Asp Phe Ser Asp Ala Asn Pro Phe Gly Glu
        115                 120                 125

Trp Gly Asp Ile Cys Ala Gln Leu Leu Ala Glu Ala Gln Glu Arg Gly
    130                 135                 140

Glu Val Leu Pro His Val Asn Pro Lys Lys Thr Gly Asp Phe Ile Val
145                 150                 155                 160

Gly Cys Phe Thr Gly Leu Gln Ala Val Ser Arg Val Thr Ser Asp Arg
                165                 170                 175

Gln Asp Leu Gly His Arg Ile Ser Val Met Trp Asn His Val Leu Pro
            180                 185                 190

Ser Ile Val Pro Ala Ser Met Leu Thr Trp Ile Glu Thr Gly Glu Glu
        195                 200                 205

Arg Ile Gly Lys Val Ala Ala Ala Ala Glu Ala Ala Glu Ala Ala Glu
```

```
            210                 215                 220
Ala Ser Glu Ala Ala Ser Asp Glu
225                 230

<210> SEQ ID NO 3
<211> LENGTH: 26
<212> TYPE: DNA
<213> ORGANISM: Streptomyces virginiae
<300> PUBLICATION INFORMATION:
<301> AUTHORS: Kinoshita, H., Tsuji, T., Ipposhi, H., Nihira, T. and
      Yamada, Y.
<302> TITLE: Characterization of Binding Sequences for Butyrolactone
      Autoregulator Receptors in Streptomycetes
<303> JOURNAL: Journal of Bacteriology
<304> VOLUME: 181
<305> ISSUE: 16
<306> PAGES: 5075-5080
<307> DATE: 1999-08
<308> DATABASE ACCESSION NUMBER: D32251
<309> DATABASE ENTRY DATE: 1994-07-19
<313> RELEVANT RESIDUES: (1)..(26)
<300> PUBLICATION INFORMATION:
<301> AUTHORS: Kinoshita, H., Tsuji, T., Ipposhi, H., Nihira, T. and
      Yamada, Y.
<302> TITLE: Characterization of Binding Sequences for Butyrolactone
      Autoregulator Receptors in Streptomycetes
<303> JOURNAL: Journal of Bacteriology
<304> VOLUME: 181
<305> ISSUE: 16
<306> PAGES: 5075-5080
<307> DATE: 1999-08
<308> DATABASE ACCESSION NUMBER: D32251
<309> DATABASE ENTRY DATE: 1994-07-19

<400> SEQUENCE: 3
agatacatac caaccggttc ttttga                                          26

<210> SEQ ID NO 4
<211> LENGTH: 110
<212> TYPE: DNA
<213> ORGANISM: Artificial sequence
<220> FEATURE:
<223> OTHER INFORMATION: Designed sequence of the CamV 35S promoter
      modified to contain the operator BARE-3 element just downstream of
      its TAT-box

<400> SEQUENCE: 4
gatatctcca ctgacgtaag ggatgacgca caatcccact atccttcgca agacccttcc     60
tctatataag agatacatac caaccggttc ttttgacggg ggactctaga              110

<210> SEQ ID NO 5
<211> LENGTH: 110
<212> TYPE: DNA
<213> ORGANISM: Artificial sequence
<220> FEATURE:
<223> OTHER INFORMATION: Designed sequence of the CaMV 35S promoter
      modified to contain the operator BARE-3 element just upstream of
      its TATA-box

<400> SEQUENCE: 5
gatatctcca ctgacgtaag ggatgacgca caatcagata cataccaacc ggttctttg     60 actatataag gaagttcatt tcatttggag agaacacggg ggactctaga              110

<210> SEQ ID NO 6
<211> LENGTH: 110
<212> TYPE: DNA
<213> ORGANISM: Artificial sequence
<220> FEATURE:
<223> OTHER INFORMATION: Designed sequence of the CaMV 35S promoter
``` modified to contain the operator BARE-3 elements just downstream
and upstream of its TATA-box

<400> SEQUENCE: 6
gatatctcca ctgacgtaag ggatgacgca caatcagata cataccaacc ggttcttttg      60
actatataag agatacatac caaccggttc ttttgacggg ggactctaga                110

<210> SEQ ID NO 7
<211> LENGTH: 136
<212> TYPE: DNA
<213> ORGANISM: Artificial sequence
<220> FEATURE:
<223> OTHER INFORMATION: Designed sequence of the CaMV 35S promoter
      modified to contain three of the operator BARE-3 elements just
      downstream and upstream of its TATA-box

<400> SEQUENCE: 7
gatatctcca ctgacgtaag ggatgacgca caatcagata cataccaacc ggttcttttg      60
actatataag agatacatac caaccggttc ttttgaagat ataccaac cggttctttt      120 gacgggggac tctaga                                                     136

<210> SEQ ID NO 8
<211> LENGTH: 27
<212> TYPE: DNA
<213> ORGANISM: Artificial sequence
<220> FEATURE:
<223> OTHER INFORMATION: Designed sequence of a backward primer
      containing the restriction enzyme BamH I recognition sequence for
      PCR amplification of the barA gene coding region to be cloned by
      cut with the enzyme

<400> SEQUENCE: 8
taggatccat aaatggcagt gcgacac                                          27

<210> SEQ ID NO 9
<211> LENGTH: 27
<212> TYPE: DNA
<213> ORGANISM: Artificial sequence
<220> FEATURE:
<223> OTHER INFORMATION: Designed sequence of a forward primer
      containing the restriction enzyme Sac Irecognition sequence for
      PCR amplification of the barA gene coding region to be cloned by
      cut with the enzyme

<400> SEQUENCE: 9
tagagctcct actcgtcgga ggcggcc                                          27

<210> SEQ ID NO 10
<211> LENGTH: 67
<212> TYPE: DNA
<213> ORGANISM: Artificial sequence
<220> FEATURE:
<223> OTHER INFORMATION: Designed sequence of one of paired oligo DNAs
      for construction of the modified CaMV 35S promoter containing
      three of the operator BARE-3 elements just downstream and upstream
      of its TATA-box

<400> SEQUENCE: 10
cggatatctc cactgacgta agggatgacg cacaatcaga tacataccaa ccggttcttt      60
tgactat                                                               67

<210> SEQ ID NO 11
<211> LENGTH: 89
<212> TYPE: DNA
<213> ORGANISM: Artificial sequence -continued

```
<220> FEATURE:
<223> OTHER INFORMATION: Designed sequence of the other of paired oligo
      DNAs for construction of the modified CaMV 35S promoter containing
      three of the operator BARE-3 elements just downstream and upstream
      of its TATA-box

<400> SEQUENCE: 11
gctctagagt cccccgtcaa aagaaccggt tggtatgtat cttcaaaaga accggttggt      60
atgtatctct tatatagtca aaagaaccg                                       89
```

METHOD OF INDUCING GENE EXPRESSION IN PLANT AND THE PLANT TREATED THEREBY

RELATED APPLICATIONS

This application is a nationalization of PCT application PCT/JP01/05096 filed Jun. 15, 2001. This application claims priority from the PCT application and Japan Application Serial No. 2000-180466 filed Jun. 15, 2000.

TECHNICAL FIELD

The present invention relates to a technique of providing a plant with a gene expression inducing system through production of a transgenic plant utilizing the gene recombination technology.

BACKGROUND ART

To provide a plant with a novel character by transferring a gene into the plant is called transformation. When the gene transferred is expressed in plant cells, the character provided manifests itself. Once the gene has been integrated in an intracellular chromosome, the character provided will be maintained stably. Such character to be newly provided by gene transfer includes, for example, resistance to diseases and agricultural chemicals and changes in metabolism. Genes for use in such transformation can freely be constructed using the current gene recombination technology. Several methods have been developed for transferring the genes constructed in such a manner into plants. For efficiently integrating a gene into a plant cell nuclear chromosome, there is available the *Agrobacterium* infection method which utilizes, as a vehicle (vector) for the gene, *Agtrobacterium*, which is a plant-infective bacterium.

The expression of a gene involves a step, called transcription, in which mRNA is transcribed upon a template, namely DNA which is the very gene containing a genetic information, and a step, called translation, in which a protein is synthesized based on the genetic information from the transcript mRNA. It is known that a gene comprises regions involved in transcriptional regulation or control in addition to the region encoding the protein information. The most basic transcriptional regulatory region is a 5' upstream region relative to the coding region and is called a promoter. The promoter differs in structure between eukaryotes, such as plants, and prokaryotes, such as bacteria. Plant promoters have a nucleotide sequence called TATA box, which is essential for initiating gene transcription, and other various regulatory sequences. For initiating transcription, RNA polymerase, which is an enzyme catalyzing the transcription in plant cells, binds to the TATA box. Various intracellular proteins called transcription factors specifically bind to the various regulatory sequences serving as targets for those factors. These transcription factors promote or inhibit the transcriptional activity of RNA polymerase and thereby control the gene expression. Thus, gene expression is under the control of such regulatory sequences. These regulatory sequences and transcription factors are also involved in induction of gene expression via the step of transcription.

To control the induction of expression of a gene transferred into a plant for transformation with respect to time and site makes it possible, with great advantage, to produce, in plants, such metabolites as otherwise will be disadvantageous to plant growth. For such purposes, the utilization of a gene expression inducing system of other organisms has often been attempted. This is because the use of a gene expression inducing system intrinsic in a plant as it is may possibly exert an unexpected influence on the metabolic system of the plant. However, it is not self-evident whether the gene expression inducing system of other organisms can be successfully given to the plant.

The regulatory system comprising an inducer, repressor and operator as found in the bacterial operon regulatory system is one of the principal gene expression inducing systems. The inducer is a low-molecular-weight compound inducing gene expression. The repressor is a receptor protein for the inducer. The operator is a regulatory sequence serving as a target for the repressor. The inducer-repressor binding and repressor-operator binding are very specific and show high levels of affinity, whereas the inducer-bound repressor cannot bind to the operator. A gene containing the operator in its promoter, namely a gene under the control of the operator, is inhibited (OFF) from being expressed when the inducer concentration is low because the repressor is bound to the operator but, as the inducer concentration increases, the repressor is released and gene expression is induced (ON).

Attempts have been reported to utilize the bacterial inducer/repressor/operator system as means for inducing gene expression in plants. For providing a plant with the characters of a repressor and operator, two genes, namely a repressor gene and a gene under the control of an operator, are transferred into the plant. For attaining expression of both genes in plant cells, it is desirable that the promoter therefor be a plant promoter. The operator is located in and near the plant promoter. By choosing the promoter, it is possible to functionally combine various characteristics of the promoter, such as gene expression intensity and tissue specificity, with the gene expression inductivity. By administering an inducer to the plant transformed in this manner, the expression of the gene placed under the control of the operator is induced at the site of administration of the inducer. As examples of the success in providing plants with such inducer/repressor/operator regulatory systems, there are reports on the systems in which tetracycline and IPTG are used as inducers [Japanese Kokai Publication Hei-06-339384 and Gatz et al., Trends in Plant Science (1998), 3, 352–358]. However, the inducer substances used in the examples so far reported have problems from feasibility points of view, for example in the aspects of environmental safety and/or cost of use.

SUMMARY OF INVENTION

In view of the above state of the art, it is an object of the present invention to provide a method of inducing gene expression in a plant to thereby control the time and site of expression induction of a gene transferred into the plant for transformation.

The present invention is a method of inducing gene expression in a plant which comprises providing the plant with characters of a repressor and operator both constituting a gene expression inducing system with an actinomycete autogenous regulatory factor as an inducer by gene transfer and administering the actinomycete autogenous regulatory factor to the transformed plant to thereby induce the expression of a gene placed under the control of the operator at a site of administration of the actinomycete autogenous regulatory factor.

In the following, the present invention is described in detail.

DETAILED DISCLOSURE OF THE INVENTION

Actinomycetes occur in soils in the highest density next to eubacteria and produce a number of physiologically active substances, such as antibiotics. As the actinomycetes, there may be mentioned, for example, the genera *Streptomyces, Micromonospora, Actinomadura, Streptosporangium, Actinoplanes, Nocardia* and *Saccharopolyspora*. The production of physiologically active substances in and the morphological differentiation of actinomycetes are controlled by endogenous microbial hormone-like substances, namely autogenous regulatory factors.

So far, three actinomycete autogenous regulatory factors are known, namely A factor in *Streptomyces griseus*, virginiae butanolide (VB) in *Streptomyces virginiae* and Inducing Material-2 in strain FRI-5 of *Streptomyces lavendulae* [Nihira, Hakko Kogaku Kaishi (1991), volume 69, 89–105].

The A factor induces the production of the antibiotic streptomycin and the streptomycin resistance in the producer and also induces the formation of conidiospores and aerial hyphae. VB induces the production, in the producer, of two species of the antibiotic virginiamycin, namely virginiamycin M and virginiamycin S, simultaneously. The Inducing Material-2 induces the conversion in antibiotic production in the producer (conversion from D-cycloserine to a nucleoside type antibiotic) and also induces the production of a blue pigment in a condition insufficient in carbon source and nitrogen source.

Like hormones, pheromones and the like as seen in other organism species, the actinomycete autogenous regulatory factors show their activity at very low concentrations, namely several nM to several score nM, in culture.

About 60% of the actinomycetes belonging to the genus *Streptomyces* are supposed to produce autogenous regulatory factors and there is the possibility that a number of unknown autogenous regulatory factors still exist.

All the known actinomycete autogenous regulatory factors has, in common, the 2-(1'-oxo or hydroxyalkyl)-3-hydoxymethyl-butyrolactone skeleton. Therefore, the known actinomycete autogenous regulatory factors are also called butyrolactone autogenous regulatory factors. In all of them, the two substituents on the lactone ring are trans in the stereostructure to each other and their absolute configurations are 2R and 3R. The factors differ in three respects, namely the alkyl side chain at position 2, the position 6, which is carbonyl or hydroxyl, and the orientation of the hydroxyl group, which is α (Inducing Material-2 type) or β (VB type).

Five VB species (A, B, C, D and E) having different alkyl side chains at position 2 are known to exist. Artificially synthesized derivatives also show the activity. The structure of the side chain at position 2 influences the intensity of the activity.

The actinomycete autogenous regulatory factors are relatively simple in structure and therefore their chemical synthesis is easy. It is also possible to axenically cultivate the producer of each factor in large amounts and separate and purify each factor from the culture thereof.

The occurrence of respective receptor proteins for A factor, VB and Inducing Material-2 in respective producers has been established and they have been named ArpA [Onaka et al., J. Bacteriol. (1995), 177, 6083–6092], BarA [Okamoto et al., J. Biol. Chem. (1995), 270, 12319–12326] and FarA [Waki et al., J. Bacteriol. (1997), 179, 5131–5137], respectively. They are composed of 276, 232 and 221 amino acids, respectively. In each of the receptor proteins, there is found, at the N terminus thereof, a helix-turn-helix motif indicative of the DNA binding ability.

The amino acid sequence of BarA, for instance, and the nucleotide sequence coding for the same are represented by SEQ ID NO:1 and SEQ ID NO:2, respectively.

The specific binding affinity between an actinomycete autogenous regulatory factor and its receptor protein is very high and the dissociation constant (Kd value) thereof is, for example, 0.7 nM for A factor/ArpA, and 1.1 nM for VB-$C_7$/BarA [Nihira, Hakko Kogaku Kaishi (1991), vol. 69, 89–105].

For example, the occurrence has been made clear of genes named barB and barX seemingly under the control of a gene expression inducing system common to the barA gene coding for the receptor protein BarA for VB at sites 3' downstream and 5' upstream thereof. Although functions of the proteins encoded by these genes are not clear yet, they are supposedly involved in virginiamycin biosynthesis in or virginiamycin resistance of the producer or in the regulatory system therefor.

As a result of an in vivo experiment [Kinoshita et al., J. Bacteriol. (1997), 179, 6986–6993], it was shown that BarA is a repressor binding to the barA and barB gene promoters and shut OFF the transcription of these genes and that VB is an inducer causing BarA to depart from the promoters to thereby turn ON the transcription of these genes. Further, as a result of an in vitro experiment [Kinoshita et al., J. Bacteriol. (1999), 181, 5075–5080], a target sequence (operator) to which BarA specifically binds was identified on each of the barA and barB genes and named BARE. It includes BARE-3 (26 bp) on the barA gene promoter, and BARE-1 (29 bp) and BARE-2 (28 bp) on the barB gene promoter. The nucleotide sequence of BARE-3, for instance, is shown under SEQ ID NO:3.

In this way, it was revealed that the actinomycete autogenous regulatory factor is involved in the gene expression inducing system in the producer. This gene expression inducing system comprises an inducer, repressor and operator. The actinomycete autogenous regulatory factor, the receptor protein for the actinomycete autogenous regulatory factor and the target sequence for the receptor protein function as the inducer, repressor and operator, respectively.

In accordance with the present invention, a plant is provided with characters of a repressor and operator both constituting a gene expression inducing system with an actinomycete autogenous regulatory factor as an inducer by gene transfer. The plant to be used in the practice of the present invention includes tobacco, corn, soy, rape, potato, cotton and the like.

To provide a plant with a character of a repressor, so referred to herein, means transformation of the plant by transfer of a repressor gene into the same. To provide a plant with a character of an operator means transformation of the plant by transfer of a gene placed under the control of an operator into the same.

In other words, in accordance with the present invention, two genes, a gene for a receptor protein for an actinomycete autogenous regulatory factor and a gene placed under the control of a target sequence for the receptor protein, are transferred into a plant for transformation thereof.

For transferring a gene for a receptor protein (repressor) for an actinomycete autogenous regulatory factor into a plant for transformation thereof, the coding region of the receptor protein gene is connected to a site 3' downstream of a promoter functioning in the plant and this is incorporated into an appropriate plasmid vector. The promoter to be used here is preferably a plant promoter.

For example, the use of the Cauliflower mosaic virus (CaMV) 35S promoter, which is known to exhibit a potent promoter activity in a variety of plant species is effective in causing potent constitutive gene expression in plants. Other plant promoters include, but are not limited to, *Agrobacterium*-derived opine (nopaline, octopine, mannopine) synthase gene promoters. Ordinary plant promoters can also be used.

To be transferred into a plant by the *Agrobacterium* infection method, for instance, a desired gene is incorporated into a plasmid vector called binary vector. The binary vector has replication systems functioning in *Escherichia coli* and *Agrobacterium*, a selective marker gene and, in addition, 25 bp nucleotide sequences called RB and LB which are essential for gene integration into a plant cell nuclear chromosome. The gene inserted between RB and LB of the binary vector, when transferred into a plant cell, is efficiently integrated into a nuclear chromosome.

For example, a binary vector for transferring the gene for the receptor protein (repressor) BarA for the actinomycete autogenous regulatory factor VB into a plant for transformation thereof can be constructed by converting the coding region of the β-glucuronidase (GUS) gene of pBI121 [Jefferson et al., EMBO J. (1987), 6, 3901–3907], which is a binary vector having a structure such that the coding region of the GUS gene is connected to a site 3' downstream of the CaMV 35S promoter, or the like binary vector to the coding region of the barA gene. When, for example, a barA gene coding region fragment having recognition sites for the restriction enzymes BamHI and SacI at both respective ends is prepared, the GUS gene coding region of the binary vector pBI121 can be converted to the barA gene coding region through the aid of the restriction enzyme BamHI and SacI recognition sites. A barA gene coding region fragment having the restriction enzyme BamHI and SacI recognition sites at both respective ends can be obtained, for example, by carrying out the PCR using chemically synthesized oligo-DNAs respectively having the nucleotide sequences shown under SEQ ID NO:8 and SEQ ID NO:9 as 5'- and 3'-PCR primers and the plasmid pET-p26k [Okamoto et al., J. Biol. Chem. (1995), 270, 12319–12326] containing the barA gene shown under SEQ ID NO:1 as a template.

For transferring a gene placed under the control of a target sequence (operator) for the actinomycete autogenous regulatory factor receptor protein into a plant for transformation thereof, the target sequence is disposed in a promoter functioning in the plant, the coding region of a desired arbitrary gene is connected to thus-modified promoter at a site 3' downstream thereof and the resulting structure is incorporated into an appropriate plasmid vector. The promoter to be used here is preferably a plant promoter.

The target sequence (operator) is desirably disposed in the vicinity of a site 3' downstream or 5' upstream of a TATA box of the promoter and it is efficient to dispose the target sequence repeatedly.

For example, a binary vector for transferring the GUS gene placed under the control of the target sequence (operator) BARE for the VB receptor protein BarA into a plant for transformation thereof can be constructed by disposing the BARE sequence in the CaMV 35S promoter of the binary vector pBI121 or the like. The enzyme encoded by the GUS gene can be easily detected through its activity and the GUS gene has no homologue in plants and, therefore, the gene is widely used as a reporter gene for experimentally detecting gene expression activity in plant cells. When, for example, the promoter has appropriate restriction enzyme recognition sites between which the target sequence (operator) is to be disposed, the disposition of the target sequence in the promoter can be attained by synthesizing a double-stranded DNA fragment comprising the nucleotide sequence between the restriction enzyme recognition sites. The disposition is also possible by the technique of site-directed mutagenesis which utilizes a chemically synthesized oligo-DNA. For disposing BARE-3 shown under SEQ ID NO:3 in the vicinity of a site 3' downstream or in the vicinity of a site 5' upstream of the TATA box of the CaMV 35S promoter, for instance, a double-stranded DNA fragment comprising, for instance, the nucleotide sequence shown under SEQ ID NO:4 or 5 may be synthesized, respectively. For disposing BARE-3 in the vicinity of a site 3' downstream and in the vicinity of a site 5' upstream of the TATA box of the CaMV 35S promoter, for instance, a double-stranded DNA fragment comprising the nucleotide sequence shown under SEQ ID NO:6, for instance, may be synthesized. For repeatedly disposing BARE-3 in the vicinity of a site 3' downstream or in the vicinity of a site 5' upstream of the TATA box of the CaMV 35S promoter, for instance, a double-stranded DNA fragment comprising the nucleotide sequence shown under SEQ ID NO:7, for instance, may be synthesized. For example, for synthesizing a double-stranded DNA fragment comprising the nucleotide sequence shown under SEQ ID NO:7 in which two BARE-3 sequences are disposed in the vicinity of a site 3' downstream of the TATA box of the CaMV 35S promoter and one BARE-3 sequence in the vicinity of a site 5' upstream of the same box, chemically synthesized oligo-DNAs comprising the nucleotide sequences shown under SEQ ID NO:10 and SEQ ID NO:11 whose 3' termini are complementary to each other over 16 bp are mixed up in a test tube and the complementary termini are allowed to anneal. DNA polymerase is added to this, and the double-stranded DNA fragment synthesized is treated with the restriction enzymes EcoRV and XbaI and then cloned in an appropriate plasmid vector.

In accordance with the present invention, the plasmid vector constructed in the above manner is transferred into a plant for transformation thereof.

In gene transfer into a plant using the *Agrobacterium* infection method, for instance, *Agrobacterium tumefaciens* or *Agrobacterium rhizogenes* is first transformed by transfer of the binary vector constructed in the above manner. For this transformation, the electroporation method or the like method is effective. The *Agrobacterium* species to be used on that occasion is required to have a function necessary for the integration of the region sandwiched between RB and LB of the binary vector in a plant cell nuclear chromosome. The transformant *Agrobacterium* can be easily selected by utilizing the function of a selective marker gene in the binary vector. A plant is infected with the transformant *Agrobacterium* thus obtained in which the binary vector containing the desired gene is transferred. For this purpose, a plant tissue section is cultured with the transformant *Agrobacterium*. Then, a callus is induced from the tissue section. On that occasion, an antibiotic for killing *Agrobacterium*, for example carbenicillin, is caused to coexist in addition to the selective marker agent. Utilizable as the selective marker gene are genes giving resistance to antibiotics, for example, kanamycin, hygromycin, bleomycin and chloramphenicol. Thus-obtained transformant callus is placed on a regeneration medium to allow plant regeneration to give a transformant plant. A transformant plant line can also be obtained from seeds of the transformant plant.

Cultured plant cell transformants can also be obtained in the same manner. In this case, however, it is not necessary to take the step of callus formation, plant body regeneration or seed formation or the like step.

In addition to the *Agrobacterium* infection method, other methods of gene transfer into plants are also available, such as the electroporation method for transferring a gene into protoplasts, the particle bombardment method which uses a gene gun and the microinjection method which comprises injecting a gene directly into cells using a microcapillary or the like. In carrying out the gene expression inducing method provided by the present invention, any of such gene transfer methods can be utilized.

In thus-obtained transformant plant, the occurrence of the gene integrated into a nuclear chromosome and of the gene product can be easily confirmed by PCR and western analysis, respectively.

While it is possible to obtain each transformant plant by transferring a gene for an actinomycete autogenous regulatory factor receptor protein (repressor) or a gene placed under the control of a target sequence (operator) for the receptor protein, it is possible to obtain a transformant plant having both genes transferred therein by the method utilizing plasmid vectors differing in selective marker gene respectively for successive transformation procedures or by the method utilizing a plasmid vector with both genes incorporated therein.

In accordance with the present invention, the actinomycete autogenous regulatory factor is administered to thus-transformed plant to thereby induce the expression of a gene placed under the control of the operator at a site of administration of the actinomycete autogenous regulatory factor.

For example, by providing tobacco plants and cultured tobacco cells with characters of the repressor BarA (receptor protein for VB) and the operator BARE-3 (one of the target sequences for BarA) which constitute a gene expression inducing system with the actinomycete *Streptomyces virginiae* autogenous regulatory factor VB as an inducer by gene transfer, and administering VB to thus-transformed tobacco plants and cultured tobacco cells, the expression of a gene placed under the control of BARE-3 could be induced at a site of administration of VB. For example, the expression of the gene placed under the control of BARE-3 could be satisfactorily induced at a VB concentration as low as 100 nM.

Owing to their relatively low molecular weights of about 200 in addition to their hydrophobic structures, the actinomycete autogenous regulatory factors can easily pass through the cell membrane. Therefore, they are very suited for use as inducers desired to be rapidly absorbed into plants.

The actinomycete autogenous regulatory factors have no toxicity to plants. For example, VB shows no toxicity to plants even at a concentration of 10 μM.

In accordance with the present invention, it is possible to produce useful transformant plants and efficiently utilize the transformant plants by choosing the gene to be placed under the control of the operator. For example, by placing a gene capable of providing a plant with fertility under the control of the operator, it is possible to control the fertility of the above transformant plant by administering an actinomycete autogenous regulatory factor to that plant. Such a plant can be utilized, for example, as a host for transformation to thereby preventing transformant plants from otherwise spreading through the natural environment.

(Explanation of Symbols)

M: Molecular weight marker

R:10 ng of the BarA protein produced using a recombinant *Escherichia coli* strain and purified 30, 21, 27: Identification numbers of the cultured tobacco cell transformant clones obtained B: Cultured tobacco cell BY2

T: The transiently transformed cultured tobacco cell protoplast obtained (Example 5)

Arrow: Position of the band indicative of the BarA protein

Figure 2:
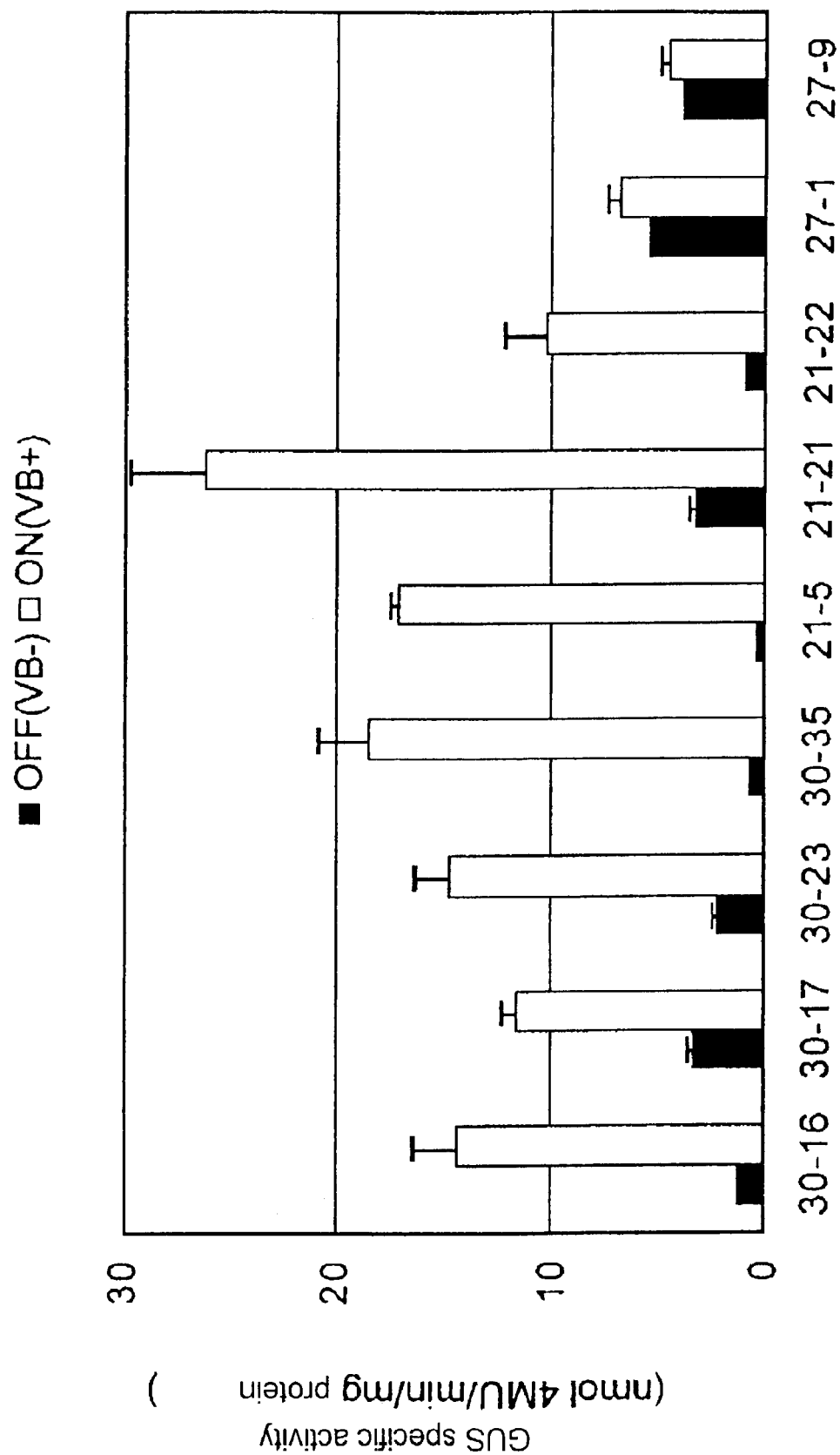

FIG. 2 shows the results of an examination as to whether the expression of the GUS reporter gene placed under the control of BARE-3 was induced in cultured tobacco cells transformed in Example 4 by providing them with the characters of the repressor BarA (receptor protein for VB) and operator BARE-3 (one of the target sequences for BarA) constituting a gene expression inducing system with the actinomycete *Streptomyces virginiae* autogenous regulatory factor VB as the inducer by gene transfer when VB was administered to the cultured tobacco cell transformants.

(Explanation of Symbols)

GUS specific activity (ordinate axis of the graph): used for the evaluation of the GUS gene expression activity (units: [nmol 4MU/min/mg protein])

30-16, 30-17, 30-23, 30-35, 21-5, 21-21, 21-22, 27-1, 27-9: Identification numbers of the cultured tobacco cell transformant clones obtained OFF (VB−): VB not added ON (VB+): VB added (final VB-$C_6$ concentration:1 μM)

Figure 3:
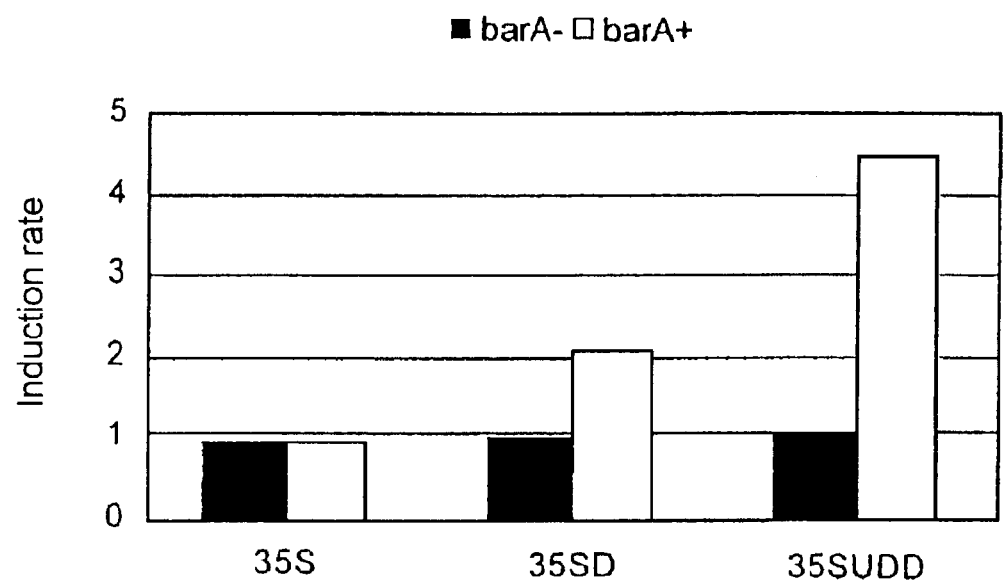

FIG. 3 shows the results of a test (results of test 1) of whether the expression of the GUS reporter gene placed under the control of BARE-3 was induced in cultured tobacco cells transformed in Example 5 by providing them with the characters of the repressor BarA (receptor protein for VB) and operator BARE-3 (one of the target sequences for BarA) constituting a gene expression inducing system with the actinomycete *Streptomyces virginiae* autogenous regulatory factor VB as the inducer by gene transfer when VB was administered to the transiently transformed cultured tobacco cells.

(Explanation of Symbols)

Induction rate (ordinate axis of the graph): The gene expression inducing activity due to VB as expressed in terms of ratio of the GUS gene expression activity when VB was added (final VB-$C_6$ concentration:1 μM, ON) to that without addition of VB (OFF) (GUS gene expression activity (ON)/ GUS gene expression activity (OFF))

Figure 4:
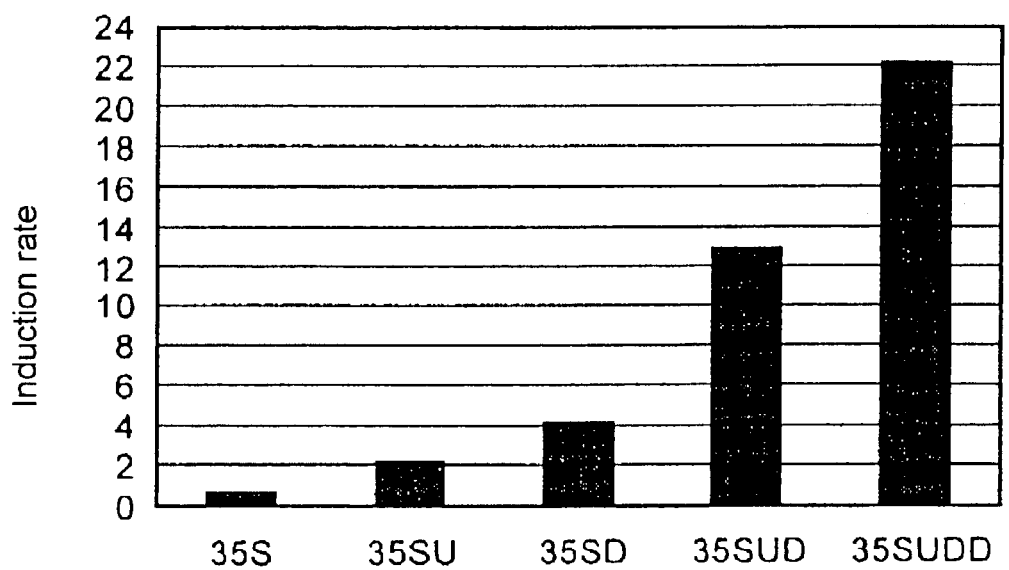

35S: When the GUS reporter gene not placed under the control of BARE-3 was used for transient transformation 35SD: When the plasmid pCaMV35SD-gus was used as the GUS reporter gene placed under the control of BARE-3 for transient transformation 35SUDD: When the plasmid pCaMV35SUDD-gus was used as the GUS reporter gene placed under the control of BARE-3 for transient transformation barA−: When the barA gene was not used for transient transformation barA+: When the barA gene was used for transient transformation FIG. 4 shows the results of a test (results of test 2) of whether the expression of the GUS reporter gene placed under the control of BARE-3 was induced in cultured tobacco cells transformed in Example 6 by providing them with the characters of the repressor BarA (receptor protein for VB) and operator BARE-3 (one of the target sequences for BarA) constituting a gene expression inducing system with the actinomycete *Streptomyces virginiae* autogenous regulatory factor VB as the inducer by gene transfer when VB was administered to the transiently transformed cultured tobacco cells.

(Explanation of Symbols)

Induction rate (ordinate axis of the graph): The gene expression inducing activity due to VB as expressed in terms of ratio of GUS gene expression activity when VB was added (final VB-$C_6$ concentration:1 µM, ON) to that without addition of VB (OFF) (GUS gene expression activity (ON)/GUS gene expression activity (OFF))

Figure 5:
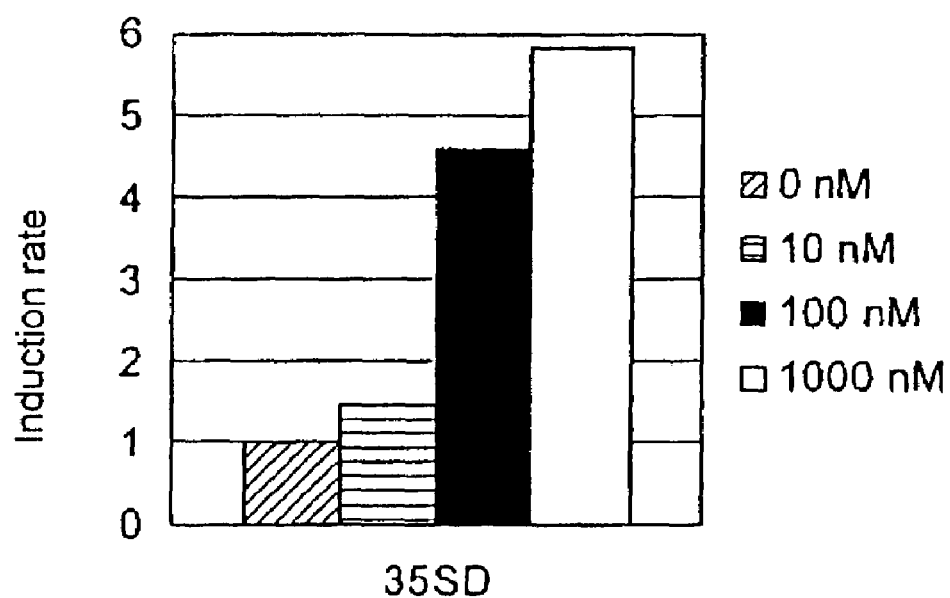

35S: When the GUS reporter gene not placed under the control of BARE-3 was used for transient transformation 35SU: When the plasmid pCaMV35SU-gus was used as the GUS reporter gene placed under the control of BARE-3 for transient transformation 35SD: When the plasmid pCaMV35SD-gus was used as the GUS reporter gene placed under the control of BARE-3 for transient transformation 35SUD: When the plasmid pCaMV35SUD-gus was used as the GUS reporter gene placed under the control of BARE-3 for transient transformation 35SUDD: When the plasmid pCaMV35SUDD-gus was used as the GUS reporter gene placed under the control of BARE-3 for transient transformation FIG. 5 shows the results of an examination as to whether the expression of the GUS reporter gene placed under the control of BARE-3 was induced in cultured tobacco cells transformed in Example 7 by providing them with the characters of the repressor BarA (receptor protein for VB) and operator BARE-3 (one of the target sequences for BarA) constituting a gene expression inducing system with the actinomycete *Streptomyces virginiae* autogenous regulatory factor VB as the inducer by gene transfer when low concentrations of VB were administered to the transiently transformed cultured tobacco cells.

(Explanation of Symbols)

Induction rate (ordinate axis of the graph): The gene expression inducing activity due to VB as expressed in terms of ratio of GUS gene expression activity when VB was added (ON) to that without addition of VB (OFF) (GUS gene expression activity (ON)/GUS gene expression activity (OFF))

35SD: When the plasmid pCaMV35SD-gus was used as the GUS reporter gene placed under the control of BARE-3 for transient transformation 0 nM: VB not added (OFF)
10 nM: VB added (ON, final VB-$C_6$ concentration:10 nM)
100 nM: VB added (ON, final VB-$C_6$ concentration:100 n)
1000 nM: VB added (ON, final VB-$C_6$ concentration:1000 nM=1 µM)

Figure 6:
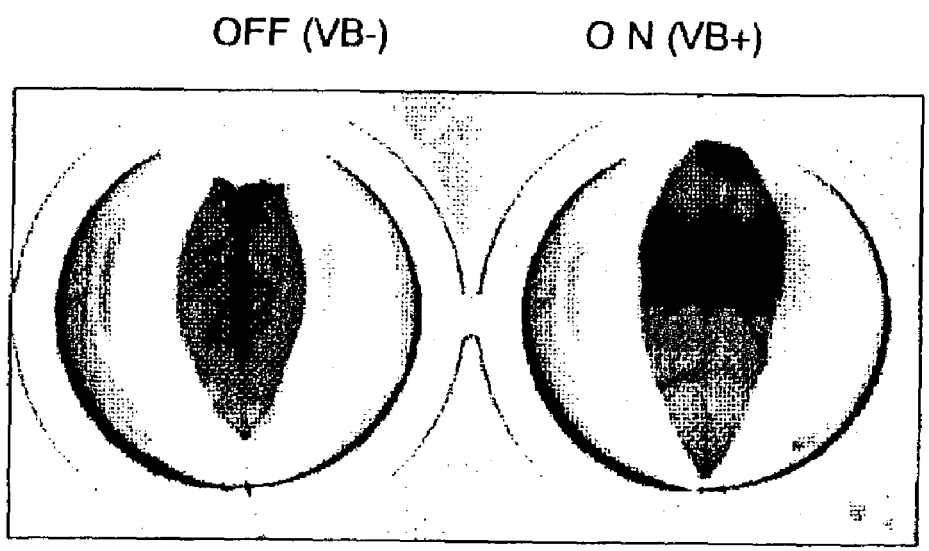

FIG. 6 shows the results of an examination as to whether the expression of the GUS reporter gene placed under the control of BARE-3 was induced in a tobacco plant transformed in Example 10 by providing the same with the characters of the repressor BarA (receptor protein for VB) and operator BARE-3 (one of the target sequences for BarA) constituting a gene expression inducing system with the actinomycete *Streptomyces virginiae* autogenous regulatory factor VB as the inducer by gene transfer when VB was administered to the transformant tobacco plant.

(Explanation of Symbols)

OFF (VB−): VB not added

ON (VB+): VB added (final VB-$C_6$ concentration:1 µM)

BEST MODES FOR CARRYING OUT THE INVENTION

The following examples illustrate the present invention in further detail. These examples are, however, by no means limitative of the scope of the present invention.

EXAMPLE 1

A plasmid vector was constructed for providing a plant with the character of the repressor BarA (receptor protein for VB) constituting a gene expression inducing system with the autogenous regulatory factor virginiae butanolide (VB) of the actinomycete *Streptomyces virginiae* as the inducer by gene transfer, namely for transferring the repressor barA gene into the plant for transformation thereof.

For this purpose, the barA gene coding region was cloned, by PCR, from the plasmid pET-p26k [Okamoto et al., J. Biol. Chem. (1995), 270, 12319–12326] containing the barA gene shown under SEQ ID NO:1. Chemically synthesized oligo-DNAs respectively comprising the nucleotide sequences shown under SEQ ID NO:8 and SEQ ID NO:9 with the restriction enzyme BamHI and SacI recognition sites introduced therein were respectively used as 5'- and 3'-primers for PCR. The fragment amplified by PCR was treated with the restriction enzymes BamHI and SacI and then inserted into the plasmid vector pBluescriptII SK(−) [GenBank accession number X52330] for cloning between the restriction enzyme BamHI recognition site and the SacI recognition site within the multicloning region (plasmid pbarA). By sequencing, it was confirmed that the barA gene coding region had been correctly cloned.

The binary vector pBI121 [Jefferson et al., EMBO J. (1987), 6, 3901–3907] having a structure such that the β-glucuronidase (GUS) gene coding region is connected to a site 3' downstream of the Cauliflower mosaic virus (CaMV) 35S promoter and having the kanamycin resistance gene as a selective marker gene was deprived of the restriction enzyme BamHI-SacI fragment containing the GUS gene coding region by treatment with the restriction enzymes BamHI and SacI. The remaining vector fragment was subjected to ligation with the restriction enzyme BamHI-SacI fragment containing the barA gene coding region as excised from the plasmid pbarA by treatment with the restriction enzymes BamHI and SacI (binary vector pBICaMV35S-barA).

A plasmid vector for transferring the repressor barA gene into a plant for transient transformation thereof was also constructed. The starting material used was the plasmid NtADHp-GUS [Nagaya et al., J. Biosci. Bioeng. (2000), 89, 231–235] having a structure such that the GUS gene coding region is connected to a site 3' downstream of the *Nicotiana tabacum* alcohol dehydrogenase (NtADH) promoter. The NtADH promoter of this plasmid is known to exhibit very potent promoter activity in tobacco.

The plasmid NtADHp-GUS was deprived of the restriction enzyme BamHI-SacI fragment containing the GUS gene coding region by treatment with the restriction enzymes BamHI and SacI. The remaining vector fragment was subjected to ligation with the restriction enzyme BamHI-SacI fragment containing the barA gene coding region as excised from the plasmid pbarA by treatment with the restriction enzymes BamHI and SacI (plasmid pNtADH-barA).

The plasmid NtADHp-GUS was deprived of the restriction enzyme BamHI-SacI fragment containing the GUS gene coding region by treatment with the restriction enzymes BamHI and SacI. The remaining vector fragment was rendered blunt-ended and then subjected to ligation (plasmid pNtADHABS).

The *Escherichia coli* DH5α strain [supE44, ΔlacU169 (Ø80, lacZΔM15), hsdR17, recA1, endA1, gyrA96, thi-1, relA1] was used as the host in a recombinant DNA experiment. As for the procedure, the standard procedure [Molecular Cloning, Maniatis et al., 1982, Cold Spring Harbor Laboratory Press, Cold Spring Harbor, N.Y.] was followed.

KOD DNA polymerase [Toyobo Co., Ltd.] was used for the PCR and the conditions employed were as described in the relevant manual.

Sequencing was carried out using a sequencer [P.E. Biosystems Japan Co., Ltd. ABI PRISM 310 Genetic Analyzer].

EXAMPLE 2

A plasmid vector was constructed for providing a plant with the character of the operator BARE-3 (one of the target sequences for the receptor protein BarA for VB) constituting a gene expression inducing system with the actinomycete *Streptomyces virginiae* autogenous regulatory factor VB as the inducer by gene transfer, namely for transferring the GUS reporter gene placed under the control of the operator BARE-3 into the plant for transformation thereof.

Two BARE-3 sequences were disposed in the vicinity of a site 3' downstream and one BARE-3 sequence was disposed in the vicinity of a site 5' upstream of the TATA box of the CaMV 35S promoter.

For this purpose, a double-stranded DNA fragment comprising the nucleotide sequence shown under SEQ ID NO:7 was synthesized which was derived from a restriction enzyme EcoRV-XbaI fragment containing the TATA box (5'-TATATAA-3') of the CaMV 35S promoter (fragment from the 762nd nucleotide to 871st nucleotide of the 871 bp CaMV 35S promoter) by substitution of BARE-3 (26 bp, shown under SEQ ID NO:3) for each of the 26 bp from the 2nd nucleotide to the 27th nucleotide 5' upstream of the TATA box and the 26 bp from the 2nd nucleotide to the 27th nucleotide 3' downstream of the TATA box and further insertion of BARE-3 (26 bp) between the 27th nucleotide and 28th nucleotide 3' downstream of the TATA box. Two chemically synthesized oligo-DNAs (100 picomoles each) respectively comprising the nucleotide sequences shown under SEQ ID NO:10 and SEQ ID NO:11 and having 3' termini complementary to each other over 16 bp were mixed with 10 μl of a TE solution and the mixture was maintained at 95° C. for 3 minutes and then cooled to room temperature. The *Escherichia coli* DNA polymerase I Klenow fragment was added to 2 μl of the above solution, the total volume was made 40 μl and the resulting reaction mixture was maintained at 37° C. for 30 minutes, the enzyme was then inactivated by phenol/chloroform treatment and the ethanol precipitate from the reaction mixture was dissolved in 5 μl of the TE solution. A 2-μl portion of this solution was treated with the restriction enzymes EcoRV and XbaI and thus-obtained restriction enzyme EcoRV-XbaI fragment was inserted into the plasmid vector pBluescriptII SK(−) for cloning between the restriction enzyme EcoRV recognition site and XbaI recognition site within the multicloning region (plasmid pBARE3UDD). Correct positioning of BARE-3 was confirmed by sequencing.

For constructing a CaMV 35S promoter with a structure having two BARE-3 sequences disposed in the vicinity of a site 3' downstream and one BARE-3 sequence in the vicinity of a site 5' upstream of the TATA box, the plasmid pBI221 [Jefferson et al., EMBO J (1987), 6, 3901–3907] having a structure such that the GUS gene coding region is connected to a site 3' downstream of the CaMV 35S promoter was treated with the restriction enzymes HindIII and EcoRV and the thus-excised fragment comprising the first nucleotide to 761st nucleotide of the CaMV 35S promoter was inserted into the plasmid pBARE3UDD between the restriction enzyme HindIII recognition site and EcoRV recognition site thereof (plasmid pCaMV35SUDD).

The binary vector pBI101HmB [Nakayama et al., Plant Physiol. (2000), 122, 1239–1247] having a structure such that the GUS gene coding region is connected to a site 3' downstream of the CaMV 35S promoter and also having the hygromycin resistance gene as a selective marker gene was deprived of the restriction enzyme HindIII-XbaI fragment containing the CaMV 35S promoter by treatment with the restriction enzymes HindIII and XbaI. The remaining vector fragment was subjected to ligation with the restriction enzyme HindIII-XbaI fragment containing the CaMV 35S promoter having a structure such that two BARE-3 sequences are disposed in the vicinity of a site 3' downstream and one BARE-3 sequence is disposed in the vicinity of a site 5' upstream of the TATA box as excised from the plasmid pCaMV35SUDD by treatment with the restriction enzymes HindIII and XbaI (binary vector pBICaMV35SUDD-gus).

A plasmid vector for transferring the GUS reporter gene placed under the control of the operator BARE-3 into a plant for transient transformation thereof was also constructed.

Two BARE-3 sequences were disposed in the vicinity of a site 3' downstream and one BARE-3 sequence was disposed in the vicinity of a site 5' upstream of the TATA box of the CaMV 35S promoter.

The plasmid pBI221 was deprived of the restriction enzyme HindIII-XbaI fragment containing the CaMV 35S promoter by treatment with the restriction enzymes HindIII and XbaI. The remaining vector fragment was subjected to ligation with the restriction enzyme HindIII-XbaI fragment containing the CaMV 35S promoter having a structure such that two BARE-3 sequences are disposed in the vicinity of a site 3' downstream and one BARE-3 sequence is disposed in the vicinity of a site 5' upstream of the TATA box as excised from the plasmid pCaMV35SUDD by treatment with the restriction enzymes HindIII and XbaI (plasmid pCaMV35SUDD-gus).

Also constructed in the same manner were plasmid vectors having a CaMV 35S promoter with a structure shown under SEQ ID NO:4 and having one BARE-3 sequence in the vicinity of a site 3' downstream of the TATA box, a structure shown under SEQ ID NO:5 and having one BARE-3 sequence in the vicinity of a site 5' upstream of the TATA box and a structure shown under SEQ ID NO:6 and having one BARE-3 sequence each in the vicinity of a site 3' downstream and in the vicinity of a site 5' upstream of the TATA box, respectively (plasmids pCaMV35SD-gus, pCaMV35SU-gus and pCaMV35SUD-gus).

EXAMPLE 3

Cultured tobacco cells were provided with the character of the repressor BarA (receptor protein for VB) constituting a gene expression inducing system with the actinomycete *Streptomyces virginiae* autogenous regulatory factor VB as the inducer by gene transfer. In other words, the repressor barA gene was transferred into cultured tobacco cells for transformation thereof.

For the gene transfer, the *Agrobacterium* infection method was employed. *Agrobacterium* was first transformed by transfer of the barA gene and cultured tobacco cells were infected with the transformant *Agrobacterium* obtained.

For the gene transfer into *Agrobacterium*, the electroporation method was used. Competent cells (50 µl) of the *Agrobacterium tumefaciens* EHA101 strain [Elizanbeth et al., J. Bacteriol. (1986), 168, 1291–1301] was mixed with 200 ng of the barA gene (Example 1, binary vector pBICaMV35S-barA) and the mixture was transferred to a cuvette (electrode-to-electrode distance 2 mm) of a gene pulser [Nippon Bio-Rad Laboratories]. Pulses were generated between the cuvette electrodes employing a voltage of 2.5 kV, an electrostatic capacity of 25 µFD and a resistance of 400 Ω. The time constant at the time of pulse generation was about 10 milliseconds. The whole contents of the pulse-loaded cuvette was spread over a LB medium agar plate containing 100 mg/l of kanamycin and the plate was allowed to stand in a dark place at 30° C. Two days later, the colonies appearing on the plate were shake-cultured in the dark at 30° C. using 5 ml of LB medium containing 100 mg/l of kanamycin for 2 days. This culture was used as transformant *Agrobacterium* culture.

Cultured tobacco BY2 cells (RIKEN Gene Bank Plant Cell Bank RPC Number 1) [Nagata et al., Methods Enzymol. (1987), 148, 34–39] were infected with the transformant *Agrobacterium* obtained. Cultured tobacco BY2 cells were subcultured at a dilution rate of about 1/50 and at about one-week intervals in the manner of shake culture in the dark at 27° C. using modified LS medium [Nagata et al., Methods Enzymol. (1987), 148, 34–39] and cells at the logarithmic growth phase (3 to 5 days after the last passage) were used for *Agrobacterium* infection. A 5-ml portion of the culture containing tobacco BY2 cells was mixed with 100 µl of the transformant *Agrobacterium* culture, the mixture was transferred to a dish and this dish was allowed to stand in the dark at 25° C. After 2 days, the *Agrobacterium* was removed from the dish by centrifugation, the remaining tobacco BY2 cells were suspended in 2 to 3 ml of modified LS medium, the suspension was spread over a modified LS medium-gellan gum plate containing 100 mg/l of kanamycin and 250 mg/l of carbenicillin, and this plate was allowed to stand in the dark at 25° C. Two to three weeks later, the calli formed on the plate were isolated and subcultured as cultured tobacco cell transformant clones in the presence of kanamycin and carbenicillin.

Whether the repressor BarA protein had been accumulated in thus-obtained cultured tobacco cell transformants was analyzed by the western blotting method.

Cells of the cultured tobacco cell transformant clones were suspended in an appropriate buffer solution for cell extraction (e.g. 0.1 M KPO4, 2 mM EDTA, 5% glycerol, 2 mM DTT, pH 7.8) and disrupted using an ultrasonic generator [KK Tomy Seiko's Handy Sonic UR-20P]. The disrupted cell-containing fluid was centrifuged at high-speed and the supernatant obtained was used as the cell extract. The protein concentration (mg/ml) in the cell extract was measured by the Bradford method [Bradford, Anal. Biochem. (1976), 72, 248–254]. An amount of the cell extract corresponding to 20 µg protein per lane was separated by SDS-PAGE (12.5% polyacrylamide gel), followed by transfer to a PVDF membrane [Nippon Bio-Rad Laboratories] and reaction with antibodies. Rabbit anti-BarA antibody [Nakano et al., J. Bacteriol. (1998), 180, 3317–3322] was used as the primary antibody and alkaline phosphatase-labeled goat anti-rabbit IgG antibody as the secondary antibody. Each reaction and washing procedure was carried out in the presence of 3% skimmed milk. Finally, the membrane was immersed in an alkaline phosphatase reaction mixture (0.017% 5-bromo-4-chloro-3-indolyl phosphate p-toluidine salt, 1 ppm nitro blue tetrazolium, 100 mM Tris-HCl, 100 mM NaCl, 5 mM $MgCl_2$, pH 9.5) for detecting a band developing a color on the membrane. The BarA protein (10 ng) produced using an *Escherichia coli* transformant and purified was used as a control sample.

Figure 1:
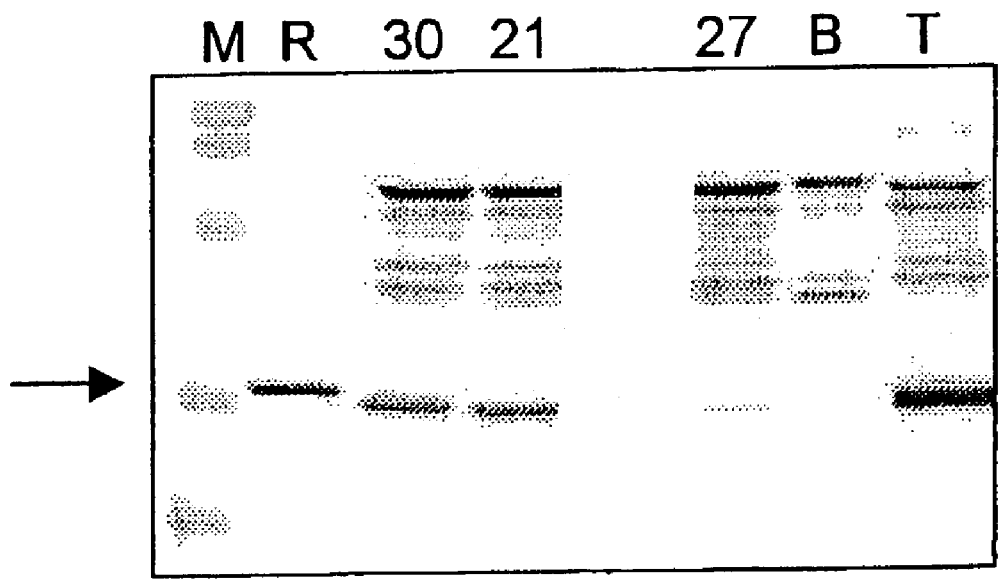
FIG. 1 shows the results of analysis, by the western blotting method, as to whether the BarA protein was accumulated in cultured tobacco cells transformed in Example 3 by providing them with the characters of the repressor BarA (receptor protein for VB) constituting a gene expression inducing system with the actinomycete *Streptomyces virginiae* autogenous regulatory factor VB as an inducer by gene transfer.

As a result, the accumulation of the BarA protein was confirmed in several cultured tobacco cell transformant clones (FIG. 1).

EXAMPLE 4

Cultured tobacco cells were provided with the characters of the repressor BarA (receptor protein for VB) and operator BARE-3 (one of the target sequences for BarA) constituting a gene expression inducing system with the actinomycete Streptomyces virginiae autogenous regulatory factor VB as the inducer by gene transfer. In other words, two genes, the repressor barA gene and the GUS reporter gene placed under the control of the operator BARE-3, were transferred into cultured tobacco cells for transformation thereof.

The GUS reporter gene placed under the control of BARE-3 (Example 2, binary vector pBICaMV35SUDD-gus) was further transferred into two clones (No. 30 and No. 21 shown in FIG. 1) seemingly indicating relatively high level acumulation of the BarA protein and one clone (No. 27 shown in FIG. 1) seemingly indicating accumulation of only a small amount of the BarA protein as judged by western analysis among the cultured tobacco cell transformant clones obtained (Example 3) by transferring the barA gene (Example 1, binary vector pBICaMV35S-barA) into cultured tobacco BY2 cells. Like in Example 3, for the gene transfer, the *Agrobacterium* infection method was employed. Cultured tobacco cell transformant clones were selected and subcultured using modified LS medium containing 20 mg/l of hygromycin, 100 mg/l of kanamycin and 250 mg/l of carbenicillin.

Whether the expression of the GUS reporter gene placed under the control of the operator BARE-3 was induced was examined by administering the inducer VB to thus-obtained cultured tobacco cell transformants.

The cultured tobacco cell transformants were subcultured at a dilution rate of about 1/25 and at about one-week intervals in the manner of shake culture in the dark at 27° C. using modified LS medium. At the time of passage, the inducer VB was added, and the GUS gene expression activity (evaluated in terms of the GUS activity per unit weight of protein, namely the GUS specific activity) of each cell extract prepared from cells cultured for 4 days was compared with that of the corresponding cell extract when VB was not added. For the addition of VB, a stock solution of VB-$C_6$ [Nihira, Hakko Kogaku Kaishi (1991), vol. 69, 89–105] (10 mg/ml methanol solution) was diluted with water at a rate of 1/50 and a 1/1000 volume of the dilution was added to the medium (final VB-$C_6$ concentration: about 1 μM). Cells were collected from 1 ml of the cell suspension by removing the supernatant by centrifugation and suspended in 500 μl of a buffer solution for cell extraction (50 mM NaH2PO4/Na2HPO4, 10 mM EDTA, 10 mM 2-mercaptoethanol, pH 7) and disrupted using an ultrasonic generator [KK Tomy Seiko's Handy Sonic UR-20P]. The disrupted cell-containing fluid was centrifuged at high-speed and the supernatant obtained was used as the cell extract. The protein concentration (mg/ml) in the cell extract was measured by the Bradford method. The GUS activity [Jefferson et al., EMBO J. (1987), 6, 3901–3907] of the cell extract was evaluated based on the amount of the fluorescent pigment 4-methylumbelliferone (4MU) formed per unit time by the enzymatic reaction, at 37° C., of GUS upon addition of 1 mM 4-methylumbelliferyl-β-D-glucuronide (4MUG) as the substrate of GUS to the cell extract. The reaction product 4 MU was quantitated by measuring the fluorescence at the wavelength 455 nm with excitation at the wavelength 365 nm, and the GUS activity (nmol 4MU/min/ml) was calculated using a calibration curve created from standard 4MU. The mean of three GUS specific activity values [nmol 4MU/min/mg protein] obtained in three independent experiments under the same experimental conditions was taken as the GUS gene expression activity under the experimental conditions mentioned above.

As a result, in a number of the cultured tobacco cell transformant clones, the GUS gene expression activity was higher when VB-$C_6$ was added (ON (VB+)) than when the same was not added (OFF (VB−)) and thus the GUS gene expression induction by VB could be observed (FIG. 2). Among the cultured tobacco cell transformant clones obtained by further transferring the GUS reporter gene placed under the control of BARE-3 (Example 2, binary vector pBICaMV35SUDD-gus) into the cultured tobacco cell transformant clones (Example 3, No. 30 and No. 21 shown in FIG. 1) seemingly indicating relatively high level accumulation of the BarA protein as obtained by transferring the barA gene (Example 1, binary vector pBICaMV35S-barA) into cultured tobacco BY2 cells, several clones (clone No. 30-derived Nos. 30-16, 30-17, 30-23 and 30-35 and clone No. 21-derived Nos. 21-5, 21-21 and 21-22) showed the ratio of the GUS gene expression activity with addition of VB-$C_6$ (ON) to that without addition thereof (OFF) (GUS gene expression activity (ON)/GUS gene expression activity (OFF)), namely the gene expression inducing activity due to VB (induction rate) of at most about 30 (induction rate≦30). Among the cultured tobacco cell transformant clones obtained by further transferring the GUS reporter gene placed under the control of BARE-3 (Example 2, binary vector pBICaMV35SUDD-gus) into the cultured tobacco cell transformant clone (Example 3, No. 27 shown in FIG. 1) seemingly indicating accumulation of only a small amount of the BarA protein as obtained by transferring the barA gene (Example 1, binary vector pBICaMV35S-barA) into cultured tobacco BY2 cells, some clones (Nos. 27-1 and 27-9) showed the gene expression inducing activity due to VB of less than 2 (induction rate≦2). Thus, the gene expression inducing activity due to VB increases as the amount of the BarA protein accumulated in the cultured tobacco cell transformants increased.

In this way, by providing cultured tobacco cells with the characters of the repressor BarA (receptor protein for VB) and operator BARE-3 (one of the target sequences for BarA) constituting a gene expression inducing system with the actinomycete autogenous regulatory factor VB as the inducer by gene transfer and administering VB to thus-obtained cultured tobacco cell transformants, the expression of the gene placed under the control of BARE-3 could be induced at the site of administration of VB.

EXAMPLE 5

Cultured tobacco cells were provided with the characters of the repressor BarA (receptor protein for VB) and operator BARE-3 (one of the target sequences for BarA) constituting a gene expression inducing system with the actinomycete *Streptomyces virginiae* autogenous regulatory factor VB as the inducer by gene transfer. In other words, two genes, the repressor barA gene and the GUS reporter gene placed under the control of the operator BARE-3, were transferred into cultured tobacco cells for transient transformation thereof.

For the gene transfer, the electroporation method was used. Therefore, a protoplast preparation was prepared from cultured tobacco cells. Cultured tobacco BY2 cells were subcultured at a dilution rate of about 1/50 and at about one-week intervals in the manner of shake culture in the dark at 27° C. using modified LS medium, and cells at the logarithmic growth phase (3 to 5 days after the last passage) were suspended in an enzyme solution (0.1% Pectolyase Y23 [KK Yakult], 1% Cellulase "Onozuka" RS [Kikkoman KK], 0.4 M mannitol, pH 5.5). The enzymatic reaction was allowed to proceed at 30° C. for 2 to 3 hours, during which the cells were dispersed by pipetting at 15-minute intervals. After confirmation under a microscope of substantially complete dispersion of spherical cells, cells in this state were used as protoplasts for gene transfer. The protoplasts were washed with 0.4 M mannitol and then suspended in a buffer solution for electroporation (5 mM 2-(N-morpholino) ethanesulfonic acid (MES), 70 mM KCl, 0.3 M mannitol) to a cell density of $3\times10^6$/ml. The barA gene (Example 1, plasmid pNtADH-barA; 50 μg), the GUS reporter gene placed under the control of BARE-3 (Example 2, plasmid pCaMV35SUDD-gus or pCaMV35SD-gus; 5 μg) and the luciferase (LUC) gene (plasmid pCaMV35S-luc [Millar et al., Plant Mol. Biol. Rep. (1992), 10, 324–337]; 1 μg) for monitoring the gene transfer efficiency were mixed up with 500 μl of the protoplast suspension and the mixture was transferred to a cuvette (electrode-to-electrode distance 4 mm) of a gene pulser [Nippon Bio-Rad Laboratories]. Pulses were generated between the cuvette electrodes employing a voltage of 200 V, an electrostatic capacity of 250 μF and a resistance of 400 Ω. The time constant at the time of pulse generation was 15 to 20 milliseconds. The protoplasts were swiftly transferred from the pulse-loaded cuvette to a dish (diameter 6 cm) and 4.5 ml of a medium (modified LS medium, 10 g/l sucrose, 0.4 M mannitol) was added thereto.

Whether the expression of the GUS reporter gene placed under the control of the operator BARE-3 was induced was examined by administering the inducer VB to thus-obtained transiently transformed cultured tobacco cell protoplasts.

The inducer VB was added (final VB-$C_6$ concentration: 1 µM) to the transiently transformed cultured tobacco cell protoplast culture in the dish, the dish was allowed to stand in the dark at 25° C. for 20 hours and then a cell extract was prepared from the protoplasts and the GUS gene expression activity thereof (evaluated in terms of the ratio of the GUS activity to the LUC activity, namely the GUS/LUC value) was compared with that found without addition of VB. The addition of VB was carried out in the same manner as in Example 4. The protoplasts were recovered from the dish, deprived of the supernatant by centrifugation and suspended in 500 µl of a buffer solution for cell extraction (0.1 M KPO4, 2 mM EDTA, 5% glycerol, 2 mM DTT, pH 7.8) and disrupted using an ultrasonic generator [KK Tomy Seiko Handy Sonic UR-20P]. The disrupted cell-containing fluid was centrifuged at high-speed and the supernatant obtained was used as the cell extract. The GUS activity (nmol 4 MU/min/ml) of the cell extract was measured in the same manner as in Example 4. The LUC activity of the cell extract was evaluated in terms of the amount of light emitted for 10 seconds as measured using a luminometer [Berthold Institut (Germany) Lumat LB9501] immediately after mixing of 100 µl of a buffer solution for cell extraction containing 470 µM luciferin [Toyo Ink Manufacturing's Pickagene] as the substrate of LUC with 20 µl of the cell extract at room temperature. The LUC activity (pmol LUC/ml) was calculated using a calibration curve created from standard LUC. The mean of three GUS/LUC values (nmol 4MU/min/pmol LUC) obtained in three independent experiments under the same experimental conditions using the same batch of the protoplast preparation was taken as the GUS gene expression activity under the experimental conditions mentioned above.

As a result, when the plasmid pCaMV35SUDD-gus or pCaMV35SD-gus was used as the GUS reporter gene placed under the control of BARE-3 for transient transformation, the GUS gene expression activity was higher when VB-$C_6$ was added (ON) than when the same was not added (OFF) and thus the GUS gene expression induction by VB could be observed (FIG. 3). The gene expression inducing activities due to VB (induction rate=GUS gene expression activity (ON)/GUS gene expression activity (OFF)) were induction rate≈5 (FIG. 3, barA+, 35SUDD) and induction rate≈2 (FIG. 3, barA+, 35SD), respectively. Thus, the gene expression inducing activity due to VB increased with the increase in the number of BARE-3 sequences. On the other hand, when the barA gene was not used for transient transformation (the control plasmid pNtADHABS containing no barA gene was used for transient transformation) (FIG. 3, barA−) and when the GUS reporter gene not under the control of BARE-3 (the control plasmid pBI221 containing no BARE-3 was used) was used for transient transformation (FIG. 3, 35S), no gene expression inducing activity due to VB was observed in any case (induction rate=1).

As a result of analysis by the same western blotting method as used in Example 3, accumulation of the repressor BarA protein was confirmed in the transiently transformed cultured tobacco cell protoplasts obtained (FIG. 1, T).

In this way, by providing cultured tobacco cells with the characters of the repressor BarA (receptor protein for VB) and operator BARE-3 (one of the target sequences for BarA) constituting a gene expression inducing system with the actinomycete autogenous regulatory factor VB as the inducer by gene transfer and administering VB to thus-obtained transiently transformed cultured tobacco cells, the expression of the gene placed under the control of BARE-3 could be induced at the site of administration of VB.

EXAMPLE 6

Cultured tobacco cells were provided with the characters of the repressor BarA (receptor protein for VB) and operator BARE-3 (one of the target sequences for BarA) constituting a gene expression inducing system with the actinomycete *Streptomyces virginiae* autogenous regulatory factor VB as the inducer by gene transfer. In other words, the repressor barA gene was transferred into cultured tobacco cells for transformation thereof and the GUS reporter gene placed under the control of the operator BARE-3 was further transferred into thus-obtained cultured tobacco cell transformant clones for transient transformation thereof.

The GUS reporter genes placed under the control of BARE-3 (Example 2, plasmid pCaMV35SUDD-gus, pCaMV35SD-gus, pCaMV35SU-gus or pCaMV35SUD-gus) were further transferred into a cultured tobacco cell transformant clone (Example 3, No. 21 shown in FIG. 1) seemingly indicating relatively high level accumulation of the BarA protein among the clones obtained by transferring the barA gene (Example 1, binary vector pBICaMV35S-barA) into cultured tobacco BY2 cells, for transient transformation of that clone. The transfer of the GUS reporter gene placed under the control of BARE-3 was carried out in the same manner as in Example 5. For monitoring the gene transfer efficiency, the LUC gene (plasmid pCaMV35S-luc) was also used for the transient transformation.

Whether the expression of the GUS reporter gene placed under the control of the operator BARE-3 was induced was examined by administering the inducer VB to thus-obtained transiently transformed cultured tobacco cell protoplasts.

Like in Example 5, the inducer VB was added (final VB-$C_6$ concentration:1 µM) to the transiently transformed cultured tobacco cell protoplast culture in the dish, the dish was allowed to stand in the dark at 25° C. for 20 hours and then a cell extract was prepared from the protoplasts and the GUS gene expression activity thereof (evaluated in terms of the ratio of the GUS activity to the LUC activity, namely the GUS/LUC value) was compared with that found without addition of VB.

As a result, when each of the plasmids pCaMV35SUDD-gus, pCaMV35SD-gus, pCaMV35SU-gus and pCaMV35SUS-gus was used as the GUS reporter gene placed under the control of BARE-3 for transient transformation, the GUS gene expression activity was higher when VB-$C_6$ was added (ON) than when the same was not added (OFF) and thus the GUS gene expression induction by VB could be observed (FIG. 4). The gene expression inducing activities due to VB (induction rate=GUS gene expression activity (ON)/GUS gene expression activity (OFF)) were induction rate≈22 (FIG. 4, 35SUDD), induction rate≈4 (FIG. 4, 35SD), induction rate≈2 (FIG. 4, 35SU) and induction rate≈13 (FIG. 4, 35SUD), respectively. Thus, the gene expression inducing activity due to VB increased with the increase in the number of BARE-3 sequences. Positioning of BARE-3 in the vicinity of a site 3' downstream of the TATA box resulted in higher gene expression inducing activity due to VB than positioning in the vicinity of a site 5' upstream thereof. On the other hand, when the GUS reporter gene not under the control of BARE-3 (the control plasmid pBI221 containing no BARE-3) was used for transient transformation (FIG. 4, 35S), no gene expression inducing activity due to VB was observed (induction rate=1).

In this way, by providing cultured tobacco cells with the characters of the repressor BarA (receptor protein for VB) and operator BARE-3 (one of the target sequences for BarA) constituting a gene expression inducing system with the actinomycete autogenous regulatory factor VB as the inducer by gene transfer and administering VB to thus-obtained transiently transformed cultured tobacco cells, the expression of the gene placed under the control of BARE-3 could be induced at the site of administration of VB.

EXAMPLE 7

Cultured tobacco cells were provided with the characters of the repressor BarA (receptor protein for VB) and operator BARE-3 (one of the target sequences for BarA) constituting a gene expression inducing system with the actinomycete *Streptomyces virginiae* autogenous regulatory factor VB as the inducer by gene transfer and whether the expression of the GUS reporter gene placed under the control of the operator BARE-3 was induced was examined by administering the inducer VB in low concentrations to thus-obtained transiently transformed cultured tobacco cells.

Like in Example 6, the GUS reporter gene placed under the control of BARE-3 (Example 2, plasmid pCaMV35SD-gus) was further transferred into a cultured tobacco cell transformant clone (Example 3, No. 21 shown in FIG. 1) seemingly indicating relatively high level accumulation of the BarA protein among the clones obtained by transferring the barA gene (Example 1, binary vector pBICaMV35S-barA) into cultured tobacco BY2 cells, for transient transformation of that clone. The inducer VB was added to thus-obtained transiently transformed cultured tobacco cell protoplast culture (final VB-$C_6$ concentrations:1 μM, 100 nM and 10 nM), cell extracts were prepared from the protoplasts allowed to stand in the dark at 25° C. for 20 hours and the GUS gene expression activities thereof (evaluated in terms of the ratio of the GUS activity to the LUC activity, namely the GUS/LUC value) was compared with that found without addition of VB.

As a result, when the plasmid pCaMV35SD-gus was used as the GUS reporter gene placed under the control of BARE-3 for transient transformation, the GUS gene expression activity was higher when VB-$C_6$ was added (ON) at each of the concentrations 1 μM, 100 nM and 10 nM than when the same was not added (OFF) and thus the GUS gene expression induction by VB could be observed (FIG. 5). The gene expression inducing activities due to VB (induction rate=GUS gene expression activity (ON)/GUS gene expression activity (OFF)) were induction rate≈5, induction rate≈4 and induction rate≈1.4, respectively. Thus, the gene expression inducing activity due to VB could be observed to a satisfactory extent at VB-$C_6$ concentrations of not less than 100 nM although it decreased with the decrease in VB concentration.

In this way, by providing cultured tobacco cells with the characters of the repressor BarA (receptor protein for VB) and operator BARE-3 (one of the target sequences for BarA) constituting a gene expression inducing system with the actinomycete autogenous regulatory factor VB as the inducer by gene transfer and administering VB at a concentration as low as 100 nM to thus-obtained transiently transformed cultured tobacco cells, the expression of the gene placed under the control of BARE-3 could be induced at the site of administration of VB to a satisfactory extent.

EXAMPLE 8

A tobacco plant was provided with the character of the repressor BarA (receptor protein for VB) constituting a gene expression inducing system with the actinomycete *Streptomyces virginiae* autogenous regulatory factor VB as the inducer by gene transfer. In other words, the repressor barA gene was transferred into a tobacco plant for transformation thereof.

For the gene transfer, the *Agrobacterium* infection method was employed. *Agrobacterium* was first transformed by transfer of the barA gene and a tobacco plant was infected with the transformant *Agrobacterium* obtained.

Tobacco (*Nicotiana tabacum* L.) was infected with the same transformant *Agrobacterium* as used in Example 3 by the leaf disc method. Square (5 to 10 mm) or disk-like leaf sections were cut from several leaves of a sterile tobacco plant grown in an MS medium [Murashige et al., Physiol. Plantarum (1962), 15, 473–498] gellan-gum pot and were immersed in sterile water in a dish, and several milliliters of the transformant *Agrobacterium* culture was admixed therewith. The leaf sections were taken out and arranged face downward on an MS callus medium (containing 2 mg/l α-naphthaleneacetic acid and 0.2 mg/l 6-benzyladenine)-gellan gum plate. The leaf sections were recovered from the plate allowed to stand in a biotron (25° C., 16 light hours, 8 dark hours) for 2 days, washed with several portions of sterile water, and arranged face downward on an MS callus medium-gellan gum plate containing 100 mg/l kanamycin and 250 mg/l carbenicillin. After 1 to 2 weeks of standing in the biotron, the leaf sections were transferred to and rearranged on an MS shooting medium (containing 0.02 mg/l α-naphthaleneacetic acid and 1 mg/l 6-benzyladenine)-gellan gum plate containing kanamycin and carbenicillin. Callus formation was confirmed around each leaf section. The plate was allowed to stand in the biotron until shoot was formed from the leaf section. The shoots formed were cut off and planted in MS medium-gellan gum pots containing kanamycin and carbenicillin. The individuals that had rooted in the pots allowed to stand in the biotron were selected, as transformant tobacco plants, in MS medium-gellan gum pots containing 20 mg/l hygromycin, 100 mg/l kanamycin and 250 mg/l carbenicillin, and maintained by subculture.

EXAMPLE 9

A tobacco plant was provided with the characters of the repressor BarA (receptor protein for VB) and operator BARE-3 (one of the target sequences for BarA) constituting a gene expression inducing system with the actinomycete *Streptomyces virginiae* autogenous regulatory factor VB as the inducer by gene transfer. In other words, the repressor barA gene was transferred into a tobacco plant for transformation thereof and the GUS reporter gene placed under the control of the operator BARE-3 was further transferred into thus-obtained transformant tobacco plant for transient transformation thereof.

The GUS reporter gene placed under the control of BARE-3 (Example 2, plasmid pCaMV35SD-gus) was further transferred into the transformant tobacco plant (Example 8) obtained by transferring the barA gene (Example 1, binary vector pBICaMV35S-barA) into tobacco (*Nicotiana tabacum* L.), for transient transformation thereof.

For the gene transfer, the electroporation method was used. Therefore, tobacco plant was treated for conversion to protoplasts. Square (5 to 10 mm) leaf sections were cut from several leaves of the tobacco plant and suspended in an enzyme solution (0.1% Pectolyase Y23 [K K Yakult], 1% Cellulase "Onozuka" RS [Kikkoman K K], 0.4 M mannitol, pH 5.5). The enzymatic reaction was allowed to proceed at room temperature for several hours. At the time point when a peeled-off layer was observed on the leaf surface, the enzyme solution was filtered through a mesh with a pore size of 70 μm, and the filtrate was centrifuged. The green mass of cells settled thereby was used as protoplasts for gene transfer. The protoplasts were washed with 0.4 M mannitol and then suspended in a buffer solution for electroporation (5 mM MES, 70 mM KCl, 0.3 M mannitol) to a cell density of $6 \times 10^6$/ml. The GUS reporter gene placed under the control of BARE-3 (Example 2, plasmid pCaMV35SD-gus; 10 μg) and the LUC gene (plasmid pCaMV35S-luc; 1 μg) for monitoring the gene transfer efficiency were mixed up with 500 μl of the protoplast suspension and the mixture was transferred to a cuvette (electrode-to-electrode distance 4 mm) of a gene pulser [Nippon Bio-Rad Laboratories]. Pulses were generated between the cuvette electrodes employing a voltage of 300 V, an electrostatic capacity of 250 μF and a resistance of 400 Ω. The time constant at the time of pulse generation was about 16 milliseconds. Two equal portions of the protoplasts were swiftly transferred from the pulse-loaded cuvette to two dishes (diameter 6 cm) and 4.75 ml of a medium (modified LS medium, 10 g/l sucrose, 0.4 M mannitol) was added to each dish.

Whether the expression of the GUS reporter gene placed under the control of the operator BARE-3 was induced was examined by administering the inducer VB to thus-obtained transiently transformed tobacco protoplasts.

The inducer VB was added (final VB-$C_6$ concentration: 1 μM) to the transiently transformed tobacco protoplast culture in one of the dishes, the dish was allowed to stand in the dark at 25° C. for 22 hours and then a cell extract was prepared from the protoplasts and the GUS gene expression activity thereof (evaluated in terms of the ratio of the GUS activity to the LUC activity, namely the GUS/LUC value) was compared with that found in the other dish without addition of VB. The addition of VB was carried out in the same manner as in Example 4. The protoplasts were recovered from each dish, deprived of the supernatant by centrifugation and suspended in 500 μl of a buffer solution for cell extraction (0.1 M KPO4, 2 mM EDTA, 5% glycerol, 2 mM DTT, pH 7.8) and disrupted using an ultrasonic generator [KK Tomy Seiko Handy Sonic UR-20P]. Each disrupted cell-containing fluid was centrifuged at high-speed and the supernatant obtained was used as the cell extract. The GUS activity and LUC activity of the cell extract were measured in the same manner as in Example 4 and Example 5, respectively. Two independent experiments were made under the same experimental conditions.

As a result, when the plasmid pCaMV35SD-gus was used as the GUS reporter gene placed under the control of BARE-3 for transient transformation, the GUS gene expression activity was higher when VB-$C_6$ was added (ON) than when the same was not added (OFF) and thus the GUS gene expression induction by VB could be observed. The gene expression inducing activity due to VB (induction rate=GUS gene expression activity (ON)/GUS gene expression activity (OFF)) was induction rate≈2 in each experiment.

In this way, by providing a tobacco plant with the characters of the repressor BarA (receptor protein for VB) and operator BARE-3 (one of the target sequences for BarA) constituting a gene expression inducing system with the actinomycete autogenous regulatory factor VB as the inducer by gene transfer and administering VB to thus-obtained transiently transformed tobacco, the expression of the gene placed under the control of BARE-3 could be induced at the site of administration of VB.

EXAMPLE 10

A tobacco plant was provided with the characters of the repressor BarA (receptor protein for VB) and operator BARE-3 (one of the target sequences for BarA) constituting a gene expression inducing system with the actinomycete *Streptomyces virginiae* autogenous regulatory factor VB as the inducer by gene transfer. In other words, two genes, the repressor barA gene and the GUS reporter gene placed under the control of the operator BARE-3, were transferred into a tobacco plant for transformation thereof.

The GUS reporter gene placed under the control of BARE-3 (Example 2, binary vector pBICaMV35SUDD-gus) was further transferred into the transformant tobacco plant (Example 8) obtained by transferring the barA gene (Example 1, binary vector pBICaMV35S-barA) into tobacco (*Nicotiana tabacum* L.). Like in Example 8, for the gene transfer, the *Agrobacterium* infection method was employed. Transformant tobacco plants were selected on MS medium containing 20 mg/l hygromycin, 100 mg/l kanamycin and 250 mg/l carbenicillin and maintained by subculture.

Whether the expression of the GUS reporter gene placed under the control of the operator BARE-3 was induced was examined by administering the inducer VB to thus-obtained transformant tobacco plant.

Lateral buds of the transformant tobacco plant were subcultured by replanting in MS medium pots supplemented with VB (final VB-$C_6$ concentration:1 μM) and leaves of the transformant tobacco plant grown in the biotron for about 3 weeks were tested for the GUS gene expression activity (evaluated in terms of the degree of staining as observed upon GUS activity staining) for comparison with the activity obtained without adding VB. In the GUS activity staining, leaves cut off were immersed in a buffer solution for cell extraction (50 mM NaH2PO4/Na2HPO4, 10 mM EDTA, 10 mM 2-mercaptoethanol, pH 7) containing 1 mM 5-bromo-4-chloro-3-indolyl-β-D-glucuronide cyclohexylammonium salt (X-gluc) as the substrate of GUS, and the reaction was allowed to proceed overnight at 37° C. The blue pigment formation in the leaves as resulting from the enzymatic reaction of GUS was observed.

As a result, the GUS gene expression activity in the transformant tobacco plant was higher when VB-$C_6$ was added (ON (VB+)) than when the same was not added (OFF (VB−)) and thus the GUS gene expression induction by VB could be observed (FIG. 6).

In this way, by providing a tobacco plant with the characters of the repressor BarA (receptor protein for VB) and operator BARE-3 (one of the target sequences for BarA) constituting a gene expression inducing system with the actinomycete autogenous regulatory factor VB as the inducer by gene transfer and administering VB to thus-obtained transformant tobacco plant, the expression of the gene placed under the control of BARE-3 could be induced at the site of administration of VB.

INDUSTRIAL APPLICABILITY

The method provided by the invention which comprises providing a plant with characters of a repressor and operator both constituting a gene expression inducing system with an actinomycete autogenous regulatory factor as an inducer by gene transfer and administering the actinomycete autogenous regulatory factor to the transformed plant to thereby induce the expression of a gene placed under the control of the operator at a site of administration of the actinomycete autogenous regulatory factor makes it possible to cause expression of a desired gene at a desired time and site, thus enabling even the production, in a plant, of a metabolite otherwise disadvantageous to the growth of the plant. The method is also useful in preventing transformant plants from spreading through the environment by controlling the fertility thereof. This method has made it possible to use an inducer excellent in characteristics and showing gene expression inducing activity in lower concentrations as compared with the other known methods of inducing gene expression in plants and, at the same time, it has opened the way for expanding the range of alternatives to be used as the inducer.

The invention claimed is:

1. A method of inducing gene expression in a plant which comprises
providing the plant with a character of a repressor and with a character of an operator by gene transfer, wherein a gene expression inducing system comprises said repressor, said operator, and virginiae butanolide as an inducer, and
administering the virginiae butanolide to the transformed plant to thereby induce, at a site of administration of the virginiae butanolide, the expression of a gene placed under the control of the operator,
wherein a gene coding for said repressor comprises a region comprising a nucleotide sequence shown under SEQ ID NO:1, or comprises a region coding for an amino acid sequence shown under SEQ ID NO:2;
a nucleotide sequence of said operator comprises a region comprising a nucleotide sequence shown under SEQ ID NO:3; and
said operator is connected to at least one site 3' downstream or 5' upstream of TATA box of a Cauliflower mosaic virus 35S promoter.

2. The method according to claim 1, wherein the coding region of the gene coding for said repressor is connected to a site 3' downstream of a plant promoter.

3. The method according to claim 2, wherein said plant promoter is a Cauliflower mosaic virus 35S promoter.

4. The method according to claim 1, wherein said operator is connected to the TATA box of said Cauliflower mosaic virus 35S promoter, in a manner shown under any of SEQ ID NO:4 through SEQ ID NO:7.

5. The method according to claim 1, wherein said gene placed under the control of the operator is a gene that provides the plant with fertility.

6. A plant transformed by the gene transfer step as recited in claim 1.

7. Tobacco *Nicotiana tabacum* L. transformed by the gene transfer step as recited in claim 1.

8. A cultured plant cell transformed by the gene transfer step as recited in claim 1.

9. A cultured tobacco cell transformed by the gene transfer step as recited in claim 1.

10. A cultured tobacco BY2 cell transformed by the gene transfer step as recited in claim 1.

11. The method according to claim 1, wherein said gene transfer comprises the step of transforming the plant with a first vector and with a second vector;
wherein said first vector comprises said operator and said gene placed under the control of said operator, in which said operator is connected to at least one site 3' downstream or 5' upstream of the TATA box of the Cauliflower mosaic virus 35S promoter;
wherein said second vector comprises said gene coding for said repressor.

12. The method according to claim 11, wherein in said second vector, the coding region of said gene coding for said repressor is connected to a site 3' downstream of a plant promoter.

13. The method according to claim 12, wherein said plant promoter is a Cauliflower mosaic virus 35S promoter.

14. The method according to claim 11, wherein in said first vector, said operator is connected to the TATA box of the Cauliflower mosaic virus 35S promoter, in a manner shown under any of SEQ ID NO:4 through SEQ ID NO:7.

15. The method according to claim 11, wherein said gene placed under the control of the operator is a gene that provides the plant with fertility.

* * * * *